United States Patent [19]

VanderSyde et al.

[11] 4,163,383
[45] Aug. 7, 1979

[54] BREATH TESTING SYSTEM

[75] Inventors: Gary L. VanderSyde, Naperville, Ill.; John Warberg, Scarborough, Canada

[73] Assignee: Alcohol Countermeasure Systems Inc., Sarnia, Canada

[21] Appl. No.: 884,120

[22] Filed: Mar. 7, 1978

[51] Int. Cl.$^2$ ............................................. G01N 27/04
[52] U.S. Cl. ..................................... 73/27 R; 422/84; 422/95
[58] Field of Search ...................... 73/23, 25, 26, 27 R; 422/84, 95, 96; 128/2 C

[56] References Cited
U.S. PATENT DOCUMENTS

| 3,600,134 | 8/1971 | Noller | 422/96 X |
|---|---|---|---|
| 3,695,848 | 10/1972 | Taguchi | 422/95 |

Primary Examiner—James J. Gill
Attorney, Agent, or Firm—Richard G. Kinney

[57] ABSTRACT

A breath tester includes an electronic detector providing an information signal with an amplitude level which varies as a function of the alcohol content in the breath under test. An anomaly detector circuit stores a signal related to the peak of the information signal, and continually compares this peak value with the instantaneous value of the information signal. When the difference between the peak signal level and the instantaneous signal level exceeds a preset amount, the output display of the breath tester is modified to indicate the analysis process has been disturbed by an anomalous chemical substance.

7 Claims, 3 Drawing Figures

BREATH TESTING SYSTEM

BACKGROUND OF THE INVENTION

Breath testers of the type which utilize an electronic detector are still relatively new and have significant advantages over the earlier chemical type detectors. Among these advantages are simplicity of use, light weight, and ease of portability and storage. Such units, for example of the type described in U.S. Pat. No. 3,877,291 have been employed in law enforcement work as "screening units," to provide an preliminary indication of a blood alcohol content. Related units have also been used to provide evidence for subsequent use in law enforcement proceedings. More recently related units have been constructed for operation by a coin-operated energizing arrangement for use, by way of example, in drinking establishments. Related background descriptions of such units are also set out in U.S. Pat. Nos. 3,764,270; 3,842,345; 3,886,786; 3,823,601; and 3,854,320, all of which are assigned to the assignee of this invention.

One drawback of such breath testers which employ an electronic detector is that the information signal can be misleading if the breath input signal comprises any anomalous chemical substance, such as acetone or ketone. Such material may be entrained in the exhaled breath of a person having diabetes, or a person adhering to one of the "fad" diets which radically change the blood chemistry, or a person who has imbibed an unusual liquid, one other than a normal alcoholic beverage. In general such an anomalous chemical substance is processed by the electronic detector to provide an information signal which can not be distinguished from an information signal having an amplitude signal denoting a high blood alcohol content.

It is therefore a primary consideration of this invention to provide a breath tester of the type having an electronic detector for developing an information signal connoting blood alcohol level, but which system is not susceptible to the production of an erroneous output by the introduction of an anomalous chemical substance as described above.

SUMMARY OF THE INVENTION

A breath tester includes an electronic detector which provides an information signal having an amplitude level which is a function of the alcohol content in the breath under test. A signal processing circuit delivers the information signal to an output display for providing an indication of the information signal amplitude. The information signal is prone to error if the breath under test provides an undesired chemical input, such as an acetone or a ketone substance, to the electronic detector.

In accordance with the present invention, an anomaly detector circuit is coupled to the signal processing circuit, for continually comparing the peak value against the instantaneous value of the information signal. Means is provided to modify the operation of the output display when the rate of decrease of the information signal provides an amplitude difference between that information signal and the peak value of the signal which indicates presence of an anomalous chemical substance in the breath under test.

THE DRAWING

In the several figures of the drawing, like reference numerals identify like components, and in that drawing.

DETAILED DESCRIPTION OF THE INVENTION

Figure 1:
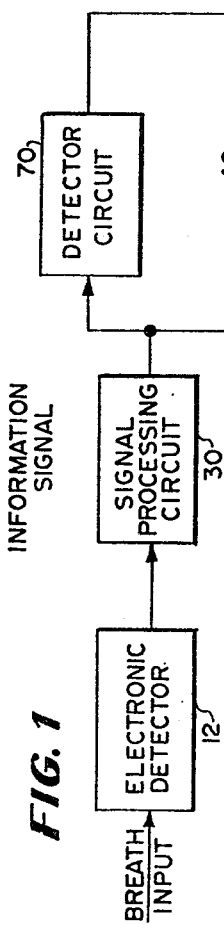
FIG. 1 is a black diagram of a breath tester system using an electronic detector and modified to incorporate the principles of this invention.

FIG. 1 shows a system for receiving a breath sample applied over a breath input line to an electronic detector 12, (e.g. the Taguchi No. 109, manufactured by Figaro Engineering) which provides an intermediate signal to a signal processing circuit 30 which in turn produces an information signal. This information signal is generally an analogue signal in which the amplitude is a function of the breath alcohol content of the person supplying the breath sample, and thus can be related to the percentage of alcohol then in the blood stream of such a person. The analogue information signal could be displayed directly on an output display 50, where such display is a conventional meter, or a pass-fail type of display in which the "fail" indication is displayed when the amplitude of the information signal exceeds a pre-set reference value. In the system of FIG. 1, the information signal is applied to an analogue-to-digital (A-to-D) converter 40, providing a digitally encoded signal on the line 48 for application to a digital display 50. Such a system is described in the earlier application of the present inventor entitled "Improved Breath Testing System," Ser. No. 818,283 filed July 22, 1977, and assigned to the assignee of this invention. A portion of the earlier invention is shown in FIG. 1, and in more detail in FIG. 2, to enable those skilled in the art to make and use the present invention with a minimum of experimentation.

Figure 2:
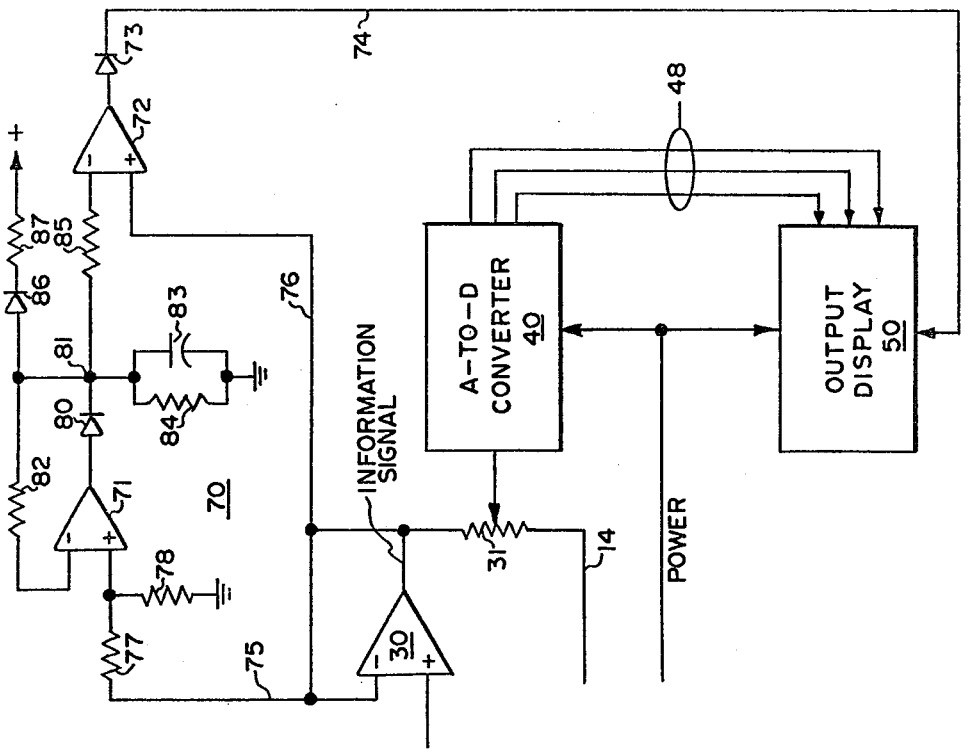
FIG. 2 is a schematic diagram, partly in block form, illustrating circuit details of the present invention.

FIG. 2 shows the signal processing circuit as a single operational amplifier (op amp) 30, although it will be apparent from the above identified application that the stage 30 is merely the output stage. The signal processing arrangement of the earlier application includes the additional stages 18, 22, 24 and 27 depicted in the signal figure of that application. To implement the present invention, it is only necessary to understand that an analogue information signal is provided as shown in FIG. 2, and a portion of such signal (depending upon the setting of potentiometer 31) is converted into a digital format for regulating the intelligence depicted on the output display 50.

Particularly in accordance with the present invention, an anomaly detector circuit 70 is provided as shown in the upper portion of FIG. 2. This detector circuit includes another operational amplifier 71 connected near its input portion, and a second operational amplifier 72 connected as a comparator to provide an output or reset signal for translation through a diode and over a line 74 to effect a reset or other modification of the display in the unit 50.

In more detail, the information signal from circuit 30 is applied over both lines 75 and 76 to the detector circuit. The signal on line 75 is passed over a series resistor 77 to the plus input terminal of op amp 71, and resistor 78 is connected between this input terminal and ground. The output side of op amp 71 is coupled through another diode 80 to a common connection point 81, and a feedback resistor 82 is coupled between this common point and the minus input connection of op amp 71. The parallel-connected combination of capacitor 83 and resistor 84 is coupled between the common connection 81 and ground. Comparator 72 has its minus input connection coupled over resistor 85 to common connection 81, and its plus input connection is coupled over line 76 to always receive the instantaneous value of the analogue information signal provided by the signal processing circuit. The common connection 81 is also coupled over a diode 86 and a resistor 87 to a point of unidirectional energizing potential, represented by the positive sign. By way of example, this can be a circuit for applying the necessary operating potential to the detector circuit 70 when the entire breath testing system is energized, has been purged and stabilized, and is considered ready for operation. Such operation, and particularly the operation and advantages of the anomaly detector circuit 70, will now be described.

Figure 3:
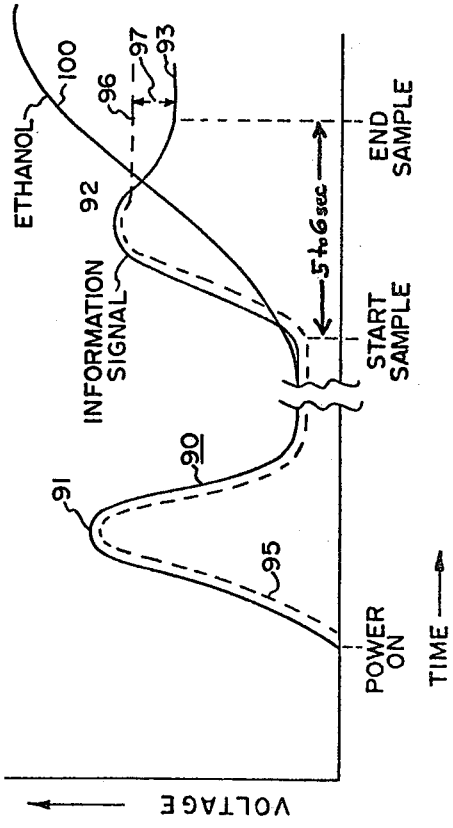
FIG. 3 is a graphic illustration useful in understanding the operation of the present invention.

FIG. 3 shows the information signal depicted by curve 90. As there shown, the system produces a first peak 91 in the analogue signal 90 when the breath tester is initially energized and is warmed up, and this peak value rapidly declines to a low stable level. This is termed "conditioning" the detector in this art. When some undesired chemical substance, such as acetone or ketone, is present in the exhaled breath of a subject under test, after the start of the sampling period the information signal amplitude rapidly rises and reaches a peak 92, which quickly declines and as shown in the drawing, has reached a level 93 at the end of the sample time. Thus, even though there is no significant alcohol content in the exhaled breath, the amplitude of the information signal may "fool" the breath testing apparatus to produce an erroneous alcoholic content indication.

A typical response to Ethanol (sometimes simply "alcohol" herein) is shown as 100. The present invention is founded on the realization that acetone sample "peaks" or changes the sign of its slope or first derivative, earlier than ethanol for this type of detector. This fact is used to prevent an "erroneous" acetone or like signal from being read as ethanol. The timing of these responses will vary somewhat depending on the detector used, the size of orifices and exposure, but it is believed that their sequence of occurrence will always be as depicted.

In accordance with the present invention the information signal appearing at the output side of stage 30 is passed over line 75 and resistor 77 to the positive input connection of op amp 71. This changes the potential at common connection 81 in the positive direction, so that the voltage across capacitor 83 goes more positive. With the instantaneous signal on line 76 also increasing in the positive direction, there is little net difference in the voltages at the input connections of comparator 72. Thus, the output voltage from comparator 72 remains low. The tracking of the information signal 90 and the voltage across capacitor 83, depicted by broken line 95, during the warm-up period is shown in the left portion of FIG. 3. After the start of the sampling period, the capacitor voltage again tracks the information signal during the positive-going increase, but after the information signal peaks and begins to decrease, the capacitor voltage remains high as represented by portion 96 of curve 95. This is accomplished by making the RC time constant of the resistor-capacitor combination 83, 84 very long with respect to the time duration of the sample period. Thus, the voltage at the minus input connection of comparator 72 remains at this higher level. When the instantaneous value of the information signal 90 decreases sufficiently, as represented by the amplitude difference 97, then the comparator output will switch and go high, causing a reset signal to be applied over line 74 to the output display. Of course the signal on line 74 need not be a reset signal. For example, if output display 50 were a meter with an angular displacement of a needle related to the amplitude of the information signal, the signal on line 74 could be utilized to displace the needle in a different direction or to a different location on the meter scale, when the comparator 72 switches.

Technical Advantages

Those skilled in the art will appreciate that the present invention obviates the erroneous display of a high alcoholic breath content of a subject under test, when in fact the exhaled breath contains only a chemical substance such as acetone or ketone and does not include any significant amount of alcohol. The detector circuit of the invention is simple and inexpensive to construct, and can be easily incorporated in existing systems such as applicant's copending application identified above. Of prime importance is the fact that the breath testing system utilizing the anomaly detector circuit obviates the characterization of an innocent subject as one having a substantial blood alcohol content, when in fact he has only some blood chemistry imbalance to produce the high level of the information signal.

By way of example only and with no intent to constrain the broad applicability of the invention, one particular anomaly detector circuit which was constructed and satisfactorily tested employed the following components and values:

| Operational Amplifiers 71, 72 | TL082 |
|---|---|
| Diodes 73,80,86 | IN914 |
| R77,R82,R85 | 1 kilohm |
| R78,R87 | 100 kilohms |
| R84 | 10 megohms |
| C83 | 10 microfarads |

In the appended claims the term "connected" means a d-c connection between two components with virtually zero d-c resistance between those components. The term "coupled" indicates there is a functional relationship between two components, with the possible interposition of other elements between the two components described as "coupled" or "intercoupled."

Although the present invention has been described in terms of a breath sampler, because that is its major, presently intended environment of use, it can also be used to test other biological gases, such as the gas evolved from a blood or urine sample.

As used herein, and in the appended claims, the term Taguchi detector means the aforementioned 109 detector and those that function similarly, such as described in U.S. Pat. No. 3,695,848, issued to Naoyoshi Taguchi.

While only a particular embodiment of the invention has been described and claimed herein, it is apparent that various modifications and alterations of the invention may be made. It is therefore the intention in the appended claims to cover all such modifications and alterations as may fall within the true spirit and scope of the invention.

What is claimed is:

1. In a biological gas tester of the type in which an electronic detector provides an information signal having an amplitude level which is a function of the alcohol content in the gas under test, including a signal processing circuit for delivering the information signal and an output display for providing an indication of the amplitude of the information signal, which signal is prone to error if the gas under test provides an undesired chemical input to the electronic detector, the improvement which comprises:

an anomaly detector circuit, coupled to the signal processing circuit, for continually comparing the maximum value of the information signal with the instantaneous value of the information signal, and means for providing a signal to modify operation of the output display when the rate of decrease of the information signal provides an amplitude difference between the instantaneous value and the maximum value of the information signal which indicates presence of an anomalous chemical substance in the gas under test.

2. A tester as claimed in claim 1, in which the anomaly detector circuit includes means for storing the peak value of the information signal, and a comparator for continually comparing the stored peak value signal with the instantaneous value of the information signal.

3. In a breath tester of the type in which an electronic detector provides an information signal having an amplitude level which is a function of the alcohol content in the breath under test, including a signal processing circuit for delivering the information signal and an output display for providing an indication of the amplitude of the information signal, which signal is prone to error if the breath under test provides an undesired chemical input to the electronic detector, the improvement which comprises:

an anomaly detector circuit, coupled to the signal processing circuit, for continually comparing the maximum value of the information signal with the instantaneous value of the information signal, and means for providing a signal to modify operation of the output display when the rate of decrease of the information signal provides an amplitude difference between the instantaneous value and the maximum value of the information signal which indicates presence of an anomalous chemical substance in the breath under test.

4. A tester as claimed in claim 3, in which the anomaly detector circuit includes means for storing the peak value of the information signal, and a comparator for continually comparing the stored peak value signal with the instantaneous value of the information signal.

5. In an ethanol gas tester of the type that may receive a gas sample to be tested, which sample may contain similar gas such as acetone, and which tester uses a detection system which produces a signal output whose amplitude peaks and turns downward for the similar gas prior to the expected peak or downward turn for ethanol, the improvement comprising circuit means for detecting the peaking or change in direction of change of the output signal during a period of time prior to the expected time that an ethanol sample would peak and producing an output indication of the fact that the similar gas is present.

6. In a biological gas tester of the type that uses a Taguchi detector, which detector responds to the presence of acetone and ethanol in similar samples and conditions, to produce a reversal of the first derivative of the amplitude signal for an acetone prior to the time that which occurs for ethanol, after the exposure of the detector to the sample, the improvement comprising:

circuit means for detecting the prior reversal and
means responsive to said circuit means for signaling the presence of the acetone.

7. In a breath tester of the type that employs a conditioned Taguchi-type detector and uses the output from that detector after a period of exposure to a breath sample to indicate the alcohol concentration of the breath, the improvement for preventing erroneous alcohol reading from the tester because of the presence of acetone or like gases in the breath sample comprising a change of direction of slope detecting circuit coupled to the detector to receive its output signal, for producing a signal if the slope of the output signal of the detector should change prior to the expiration of the period, and means responsive to that signal to indicate the presence of the acetone or like.

* * * * *